United States Patent
Tyagi et al.

(10) Patent No.: US 11,234,101 B2
(45) Date of Patent: Jan. 25, 2022

(54) DETERMINING AN ORIENTATION AND BODY LOCATION OF A WEARABLE DEVICE

(71) Applicant: MOTOROLA MOBILITY LLC, Chicago, IL (US)

(72) Inventors: Vivek K. Tyagi, Chicago, IL (US); Joseph V. Nasti, Chicago, IL (US); Sudhir Vissa, Bensenville, IL (US); Douglas A. Lautner, Round Lake, IL (US)

(73) Assignee: Motorola Mobility LLC, Chicago, IL (US)

( * ) Notice: Subject to any disclaimer, the term of this patent is extended or adjusted under 35 U.S.C. 154(b) by 409 days.

(21) Appl. No.: 15/713,051

(22) Filed: Sep. 22, 2017

(65) Prior Publication Data
US 2019/0098452 A1   Mar. 28, 2019

(51) Int. Cl.
| | |
|---|---|
| H04W 4/02 | (2018.01) |
| G08C 23/04 | (2006.01) |
| H04B 17/318 | (2015.01) |
| A61B 5/00 | (2006.01) |
| H04B 17/27 | (2015.01) |
| A61B 5/024 | (2006.01) |

(52) U.S. Cl.
CPC ........... *H04W 4/026* (2013.01); *G08C 23/04* (2013.01); *H04B 17/27* (2015.01); *H04B 17/318* (2015.01); *A61B 5/02438* (2013.01); *A61B 5/4504* (2013.01); *A61B 5/681* (2013.01); *A61B 5/6844* (2013.01)

(58) Field of Classification Search
CPC ..... H04W 4/026; H04B 17/27; H04B 17/318; G08C 23/04; A61B 5/02438; A61B 5/4504; A61B 5/681; A61B 5/6844
USPC ........................................................ 702/150
See application file for complete search history.

(56) References Cited

U.S. PATENT DOCUMENTS

| | | | | |
|---|---|---|---|---|
| 10,126,837 | B1* | 11/2018 | Bergstrom | G06F 1/1694 |
| 2009/0079701 | A1* | 3/2009 | Grosskopf, Jr. | G06F 1/1626 |
| | | | | 345/173 |
| 2009/0265105 | A1* | 10/2009 | Davis | G01C 21/20 |
| | | | | 701/300 |
| 2012/0206332 | A1* | 8/2012 | Yonemoto | G06F 1/1694 |
| | | | | 345/156 |

(Continued)

OTHER PUBLICATIONS

Burns, Enid, "Universal Earphones detect left and right ear placement", http://newatlas.com/universal-earphones-earbuds-left-right-channel/21331/, Feb. 5, 2012.

*Primary Examiner* — Michael P Nghiem
(74) *Attorney, Agent, or Firm* — Isidore PLLC (57) ABSTRACT

A method, a system, and a computer program product for configuring output devices of a wearable device based on a detected orientation and body location of the wearable device. The method includes measuring at least one orientation input from at least one orientation module of a wearable device. The method further includes analyzing, via a processor of the wearable device, the at least one orientation input to determine a body location of the wearable device and a current orientation of the wearable device at the body location. The method further includes configuring at least one output device of the wearable device for operation in the current orientation at the body location.

20 Claims, 7 Drawing Sheets

(56) References Cited

U.S. PATENT DOCUMENTS

| | | | |
|---|---|---|---|
| 2013/0120106 A1* | 5/2013 | Cauwels | G06F 1/163 340/3.1 |
| 2013/0120459 A1* | 5/2013 | Dickinson | G06F 1/163 345/650 |
| 2013/0222270 A1* | 8/2013 | Winkler | H04M 1/0233 345/173 |
| 2015/0123889 A1* | 5/2015 | Willis | G06F 3/013 345/156 |
| 2015/0128094 A1* | 5/2015 | Baldwin | G06F 3/017 715/863 |
| 2015/0185836 A1* | 7/2015 | Slonneger | G06F 3/014 345/156 |
| 2015/0199950 A1* | 7/2015 | Heiman | H04R 1/1083 381/71.1 |
| 2015/0355677 A1* | 12/2015 | Breedvelt-Schouten | G02B 27/0093 345/419 |
| 2017/0003765 A1* | 1/2017 | Shedletsky | G06F 1/163 |
| 2017/0345399 A1* | 11/2017 | Lee | G06F 1/1626 |
| 2018/0317770 A1* | 11/2018 | Ortega | A61B 5/0488 |
| 2019/0133488 A1* | 5/2019 | Meftah | A61B 5/318 |

\* cited by examiner

Left hand upright orientation

FIG. 3B

Left hand reverse orientation

FIG. 3C

Right hand upright orientation

FIG. 3D

Right hand reverse orientation

DETERMINING AN ORIENTATION AND BODY LOCATION OF A WEARABLE DEVICE

BACKGROUND

1. Technical Field

The present disclosure generally relates to wearable electronic devices and in particular to a method for configuring output devices of a wearable electronic device.

2. Description of the Related Art

Wearable devices, such as smart watches, headphones, and fitness trackers, are commonly used to provide users with access to content. However, in many cases wearable devices must be configured for a particular orientation (e.g., left-handed orientation or right-handed orientation) before they may be properly used. If a wearable device is worn in an improper orientation, usability of the wearable device may be hindered (e.g., text on a screen of the wearable device may appear upside-down). Existing solutions enable a user of a wearable device to manually select an orientation of the wearable device. For example, a user may establish which wrist a wearable device is attached to in a corresponding settings menu of the wearable device. Another existing solution uses gyroscopic sensors to estimate a wearable device's orientation on the body of a user. However, these solutions are prone to errors and require multiple continuous measurements that cause significant battery drain of the wearable device.

BRIEF DESCRIPTION OF THE DRAWINGS

The description of the illustrative embodiments is to be read in conjunction with the accompanying drawings. It will be appreciated that for simplicity and clarity of illustration, elements illustrated in the figures have not necessarily been drawn to scale. For example, the dimensions of some of the elements are exaggerated relative to other elements. Embodiments incorporating teachings of the present disclosure are shown and described with respect to the figures presented herein, in which.

DETAILED DESCRIPTION

The illustrative embodiments provide a method, a system, and a computer program product for configuring output devices of a wearable device based on a detected orientation and body location of the wearable device. The method includes measuring at least one orientation input via at least one orientation module of a wearable device. The method further includes analyzing, via a processor of the wearable device, the at least one orientation input to determine a body location of the wearable device and a current orientation of the wearable device at the body location. The method further includes configuring at least one output device of the wearable device for operation in the current orientation at the body location.

The above contains simplifications, generalizations and omissions of detail and is not intended as a comprehensive description of the claimed subject matter but, rather, is intended to provide a brief overview of some of the functionality associated therewith. Other systems, methods, functionality, features, and advantages of the claimed subject matter will be or will become apparent to one with skill in the art upon examination of the following figures and the remaining detailed written description. The above as well as additional objectives, features, and advantages of the present disclosure will become apparent in the following detailed description.

In the following description, specific example embodiments in which the disclosure may be practiced are described in sufficient detail to enable those skilled in the art to practice the disclosed embodiments. For example, specific details such as specific method orders, structures, elements, and connections have been presented herein. However, it is to be understood that the specific details presented need not be utilized to practice embodiments of the present disclosure. It is also to be understood that other embodiments may be utilized and that logical, architectural, programmatic, mechanical, electrical and other changes may be made without departing from the general scope of the disclosure. The following detailed description is, therefore, not to be taken in a limiting sense, and the scope of the present disclosure is defined by the appended claims and equivalents thereof.

References within the specification to "one embodiment," "an embodiment," "embodiments", or "one or more embodiments" are intended to indicate that a particular feature, structure, or characteristic described in connection with the embodiment is included in at least one embodiment of the present disclosure. The appearance of such phrases in various places within the specification are not necessarily all referring to the same embodiment, nor are separate or alternative embodiments mutually exclusive of other embodiments. Further, various features are described which may be exhibited by some embodiments and not by others.

Similarly, various aspects are described which may be aspects for some embodiments but not other embodiments.

The terminology used herein is for the purpose of describing particular embodiments only and is not intended to be limiting of the disclosure. As used herein, the singular forms "a", "an", and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Moreover, the use of the terms first, second, etc. do not denote any order or importance, but rather the terms first, second, etc. are used to distinguish one element from another.

It is understood that the use of specific component, device and/or parameter names and/or corresponding acronyms thereof, such as those of the executing utility, logic, and/or firmware described herein, are for example only and not meant to imply any limitations on the described embodiments. The embodiments may thus be described with different nomenclature and/or terminology utilized to describe the components, devices, parameters, methods and/or functions herein, without limitation. References to any specific protocol or proprietary name in describing one or more elements, features or concepts of the embodiments are provided solely as examples of one implementation, and such references do not limit the extension of the claimed embodiments to embodiments in which different element, feature, protocol, or concept names are utilized. Thus, each term utilized herein is to be provided its broadest interpretation given the context in which that term is utilized.

Figure 1:
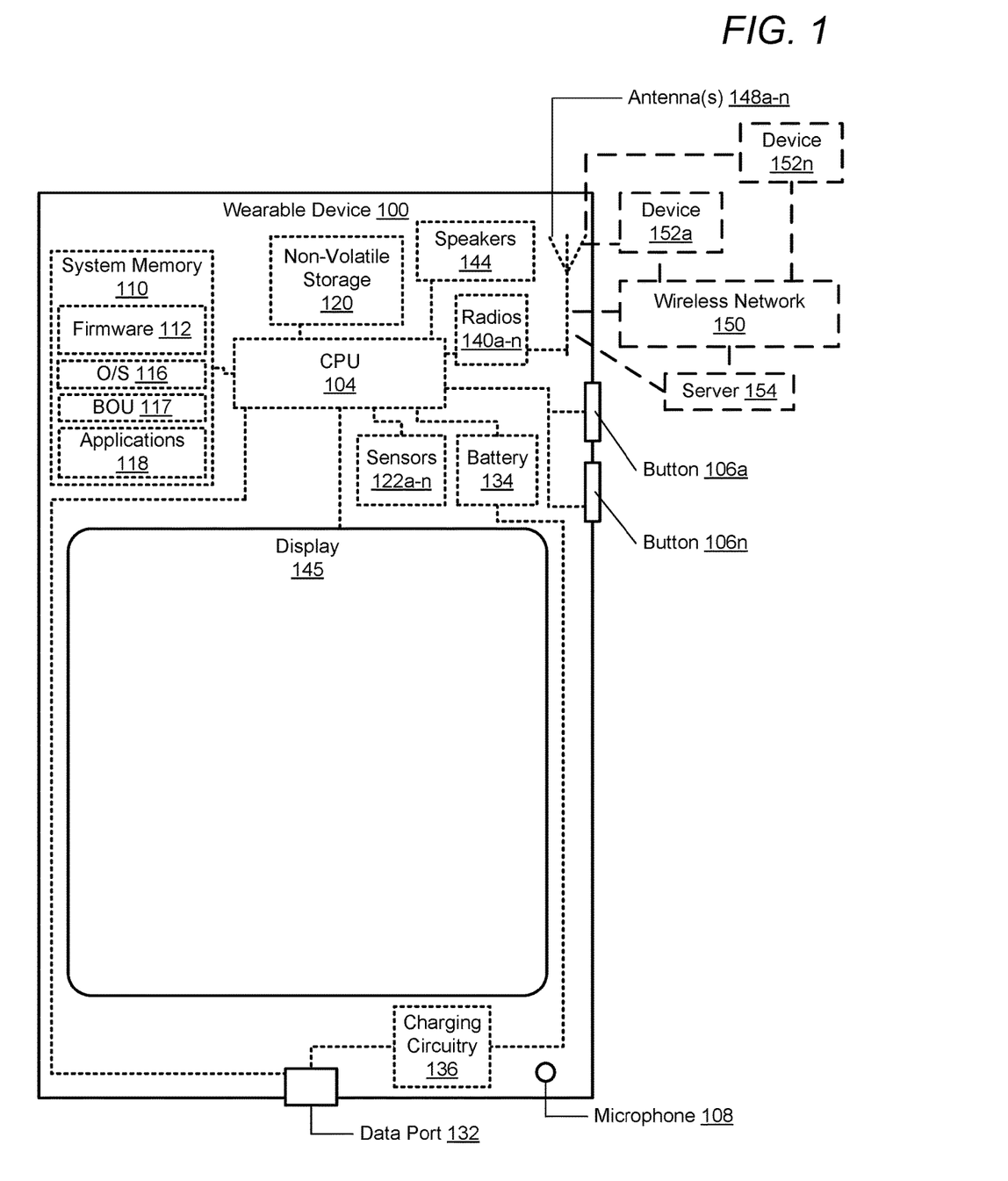
FIG. 1 illustrates a wearable device within which certain aspects of the disclosure can be practiced, in accordance with one or more embodiments.

Those of ordinary skill in the art will appreciate that the hardware components and basic configuration depicted in the following figures may vary. For example, the illustrative components within wearable device 100 are not intended to be exhaustive, but rather are representative to highlight components that can be utilized to implement the present disclosure. For example, other devices/components may be used in addition to, or in place of, the hardware depicted. The depicted example is not meant to imply architectural or other limitations with respect to the presently described embodiments and/or the general disclosure.

Within the descriptions of the different views of the figures, the use of the same reference numerals and/or symbols in different drawings indicates similar or identical items, and similar elements can be provided similar names and reference numerals throughout the figure(s). The specific identifiers/names and reference numerals assigned to the elements are provided solely to aid in the description and are not meant to imply any limitations (structural or functional or otherwise) on the described embodiments.

Now turning to FIG. 1, there is illustrated an example wearable device 100 within which one or more of the described features of the various embodiments of the disclosure can be implemented. In at least one embodiment, wearable device 100 can be any electronic device that may be attached to a body of a subject/user. Example wearable devices can include, but are not limited to, wrist/smart watches, headphones, body cameras, and fitness trackers. Wearable device 100 includes at least one processor or central processing unit (CPU) 104. CPU 104 is coupled to non-volatile storage 120 and system memory 110, within which firmware 112, operating system (OS) 116, body orientation utility (BOU) 117, and applications 118 can be stored for execution by CPU 104. According to one aspect, BOU 117 executes within wearable device 100 to perform the various methods and functions described herein. In one or more embodiments, BOU 117 configures output devices and/or the orientation and/or presentation of I/O user interfaces presented on one or more output devices of wearable device 100 based on a detected orientation and body location of wearable device 100. For simplicity, BOU 117 is illustrated and described as a stand-alone or separate software/firmware/logic component, which provides the specific functions and methods described below. However, in at least one embodiment, BOU 117 may be a component of, may be combined with, or may be incorporated within firmware 112, or OS 116, and/or within one or more of applications 118.

As shown, wearable device 100 may include input devices, such as hardware buttons 106a-n, and output devices, such as display 145, that enable a user to interface with wearable device 100. Hardware buttons 106a-n are selectable buttons that are used to receive manual/tactile input from a user to control specific operations of wearable device 100 and/or of applications executing thereon. In at least one embodiment, hardware buttons 106a-n may also include, or may be connected to, one or more sensors (e.g. a fingerprint scanner) and/or may be pressure sensitive.

Hardware buttons 106a-n may also be directly associated with one or more functions of a graphical user interface (not pictured) and/or functions of an OS, application, or hardware of wearable device 100. In at least one embodiment, hardware buttons 106a-n may include a keyboard. Speakers 144 are used to output audio signals. In at least one embodiment, speakers 144 include at least one transducer capable of outputting signals. The signals may include, but are not limited to, radio frequency (RF) signals, audio signals in the human audible range, and/or ultrasound signals. Wearable device 100 also includes microphone 108. In at least one embodiment, microphone 108 includes at least one audio receiver for capturing audio signals emitted by speakers 144. In another embodiment, microphone 108 may be used to receive spoken input/commands from a user. In some embodiments, wearable device 100 can also include cameras (not illustrated) for capturing images and/or video.

Display 145 is capable of displaying text, media content—including images and video, and/or a graphical user interface (GUI) associated with or generated by firmware and/or software executing on wearable device 100. The GUI can be rendered by CPU 104 for viewing on display 145, in at least one embodiment, or can be rendered by a graphics processing unit (GPU) (not separately shown), in another embodiment. In at least one embodiment, display 145 is a touch screen that is capable of receiving touch/tactile input from wearable device 100. In at least one embodiment, wearable device 100 can include a plurality of virtual buttons or affordances that operate in addition to, or in lieu of, hardware buttons 106a-n. For example, wearable device 100 can be equipped with a touch screen interface and provide, via a GUI, a virtual keyboard or other virtual icons for user interfacing therewith.

CPU 104 is also coupled to sensors 122a-n. Sensors 122a-n can include, but are not limited to, at least one of: infrared (IR) emitters, IR receivers, time-of-flight emitters/receivers, structured light emitters/receivers, thermal sensors, light sensors, motion sensors, and/or accelerometers, heart rate sensors, proximity sensors, and camera/image sensors.

Wearable device 100 also includes data port 132 (e.g., a universal serial bus (USB) port), battery 134, and charging circuitry 136. Data port 132 can operate as a charging port that receives power via an external charging device (not pictured) for charging battery 134 via charging circuitry 136. Data port 132 may also function as one of an input port, an output port, and a combination input/output port for exchanging data via a serial or parallel connection with another device. Battery 134 may include a single battery or multiple batteries for providing power to components of wearable device 100. In at least one embodiment, battery 134 may include at least one battery that is removable and/or replaceable by an end user. In another embodiment, battery 134 may include at least one battery that is permanently secured within/to wearable device 100.

Wearable device 100 may also include one or more wireless radios 140a-n and can include one or more antenna(s) 148a-n that enable wearable device 100 to wirelessly connect to, and transmit and receive voice and/or data communication to/from, one or more other devices, such as devices 152a-n and server 154. As a wireless device, wearable device 100 can transmit data over a wireless network 150 (e.g., a Wi-Fi network, cellular network, Bluetooth® network (including Bluetooth® low energy (BLE) networks), a wireless ad hoc network (WANET), or personal area network(PAN)). In at least one embodiment, wearable device 100 may be further equipped with an infrared (IR) device (not pictured) for communicating with other devices using an IR connection. In another embodiment, wireless radios 140a-n may include a short-range wireless device, including, but not limited to, a near field communication (NFC) device. In still another embodiment, wearable device 100 may communicate with one or more other device(s) using a wired or wireless USB connection.

Figure 2:
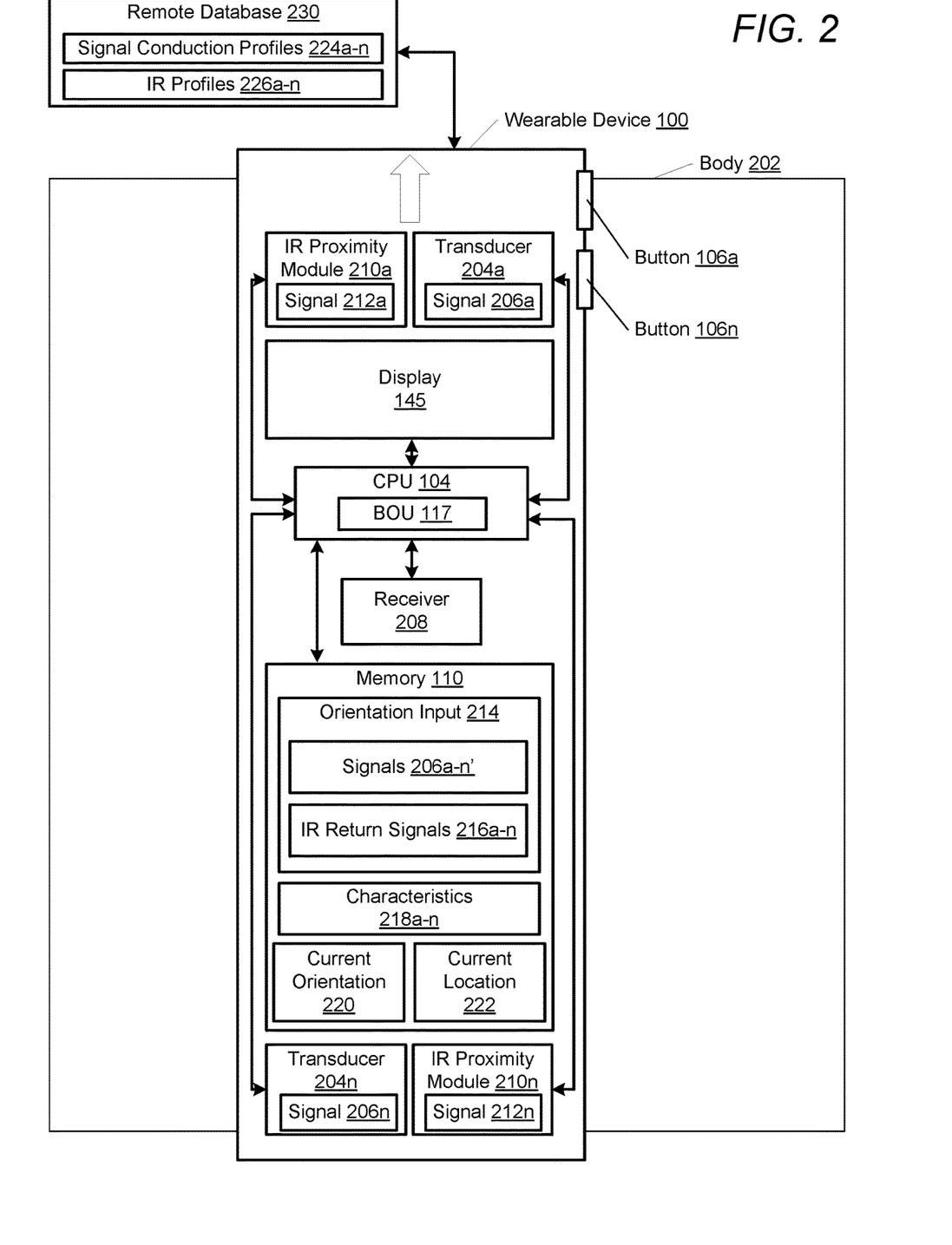
FIG. 2 illustrates an example wearable device that is configured to detect its current orientation and body location, in accordance with one or more embodiments of the disclosure.

FIG. 2 is a block diagram illustrating additional functional components within example wearable device 100, in accordance with one or more embodiments of the present disclosure. Wearable device 100 is configured to detected a current orientation and current body location and to configure input and/or output devices of the wearable device for operation at the detected current orientation and current body location. Wearable device 100 is an electronic device that is worn on the body of a subject (e.g., a person). In the illustrated embodiment, wearable device 100 is worn on body 202 at a wrist (or lower arm area) of a subject. In another embodiment, wearable device 100 may be worn at another body location of a subject, such as an arm, hand, leg, or chest, without limitation. As illustrated, wearable device 100 includes CPU 104, memory 110, and display 145. CPU 104 executes BOU 117 to perform the various functional features of the disclosure described herein. CPU 104 receives orientation input 214 via at least one orientation module, such as transducers 204a-n and/or IR proximity modules 210a-n, and CPU 104 analyzes orientation input 214 to determine current orientation 220 and current location 222 of wearable device 100 on the body 202 (skin) of a subject. In one or more embodiments, CPU 104 compares orientation input 214 to at least one orientation profile, such as signal conduction profiles 224a-n and/or IR profiles 226a-n, to determine current orientation 220 (e.g., upright orientation or reverse orientation) and current location 222 (e.g, left hand or right hand) of wearable device 100 on body 202 of a subject. Each orientation profile includes and/or describes at least one signature of at least one return signal that is associated with at least one orientation module and further associates the signature(s) with a particular body location and/or orientation of wearable device 100. For example, CPU 104 may compare orientation input 214 to a plurality of orientation profiles to determine the current orientation 220 of wearable device 100 as being an upright orientation and a current location 222 as the left wrist. It should be noted that current location 222 can be any location on the body of a subject including, but not limited to: an ankle, chest, or ear of a subject.

Figure 3A:
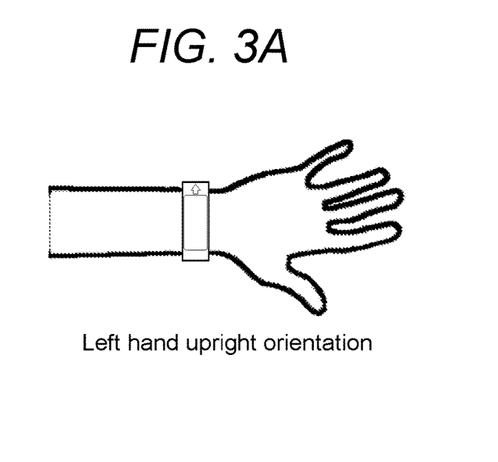
FIG. 3A, illustrates an example wearable device that is worn on a wrist of a subject in a left hand upright orientation in accordance with one or more embodiments.
Figure 3B:
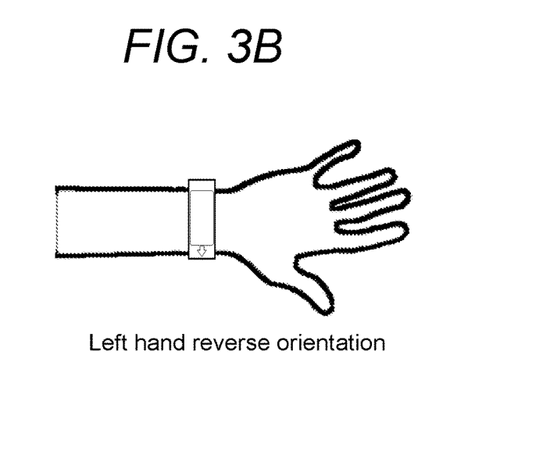
FIG. 3B illustrates an example wearable device that is worn on a wrist of a subject in a left hand reverse orientation in accordance with one or more embodiments.
Figure 3C:
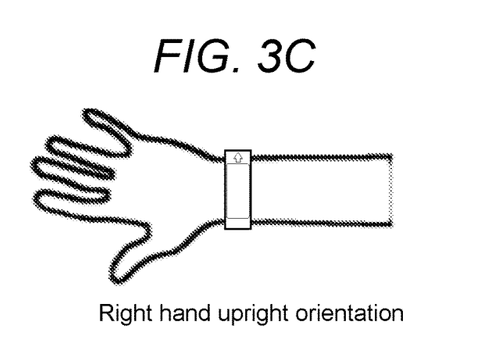
FIG. 3C illustrates an example wearable device that is worn on a wrist of a subject in a right hand upright orientation in accordance with one or more embodiments.
Figure 3D:
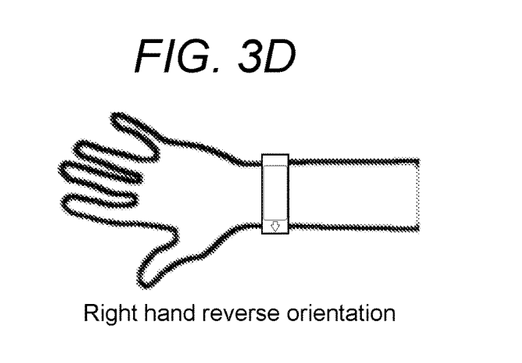
FIG. 3D illustrates an example wearable device that is worn on a wrist of a subject in a right hand reverse orientation in accordance with one or more embodiments.

Referring now to FIGS. 3A-D, there is illustrated four orientations in which wearable device 100 may be worn. FIG. 3A illustrates wearable device 100 worn in the left hand upright orientation. FIG. 3B illustrates wearable device 100 worn in the left hand reverse (i.e., downwards) orientation. FIG. 3C illustrates wearable device 100 worn in the right hand upright orientation. FIG. 3D illustrates wearable device 100 worn in the right hand reverse (downward) orientation.

Referring again to FIG. 2, in at least one embodiment, orientation profiles (signal conduction profiles 224a-n and IR profiles 226a-n) are stored within a memory and/or storage (e.g., memory 110) of wearable device 100. In other embodiments, CPU 104 accesses and/or retrieves orientation profiles from remote database 230. For example, orientation profiles may be retrieved on-demand during the detection of current orientation 220 and current location 222 by wearable device. In another embodiment, orientation profiles are retrieved during a setup or configuration of wearable device 100. In another embodiment, orientation profiles are retrieved at a predetermined time (e.g., while wearable device is charging). In another embodiment, orientation profiles are retrieved in response to receiving a request from a user of wearable device 100 to retrieve and/or update orientation profiles stored in memory 110. It should also be noted that, in one or more embodiments, orientation profiles may be periodically synced between remote database 230 and wearable device 100. In at least one embodiment, remote database 230 may be a server (e.g., server 154) that is accessible to wearable device 100 and/or other wearable devices (not illustrated) via a network. In another embodiment, remote database 230 may be hosted within at least one virtual server, such as a cloud service.

In at least one embodiment, the at least one orientation module of wearable device 100 includes at least one transducer 204a-n and receiver 208 for determining a current orientation 220 and current location 222 of wearable device 100 on body 202 via bone conduction detection. In another embodiment, the at least one orientation module of wearable device 100 includes a plurality of IR proximity modules 210a-n for determining a current orientation 220 and current location 222 of wearable device 100 on body 202 via infrared light detection. In one or more embodiments, the at least one orientation module of wearable device 100 includes (i) both transducers 204a-n, and receiver 208 and (ii) IR proximity modules 210a-n. In those latter embodiments, CPU 104 may determine current orientation 220 and current location 222 of wearable device 100 on body 202 using one or both of bone conduction detection methods and infrared light detection methods, as described in greater detail below.

Bone Conduction Detection

In at least one embodiment, wearable device 100 includes at least one transducer 204a-n and at least one receiver 208 and utilizes these two components to determine a current orientation 220 and current location 222 of wearable device 100 on body 202 via bone conduction detection. In the illustrated embodiment, transducer 204a is located at a top side of wearable device 100, receiver 208 is located in a center of wearable device 100, and transducer 204n is located at a bottom side of wearable device. In the illustrated embodiment, receiver 208 and transducers 204a-n are physically located on an underside of wearable device 100. In the illustrated embodiment, when wearable device 100 is being properly worn, receiver 208 and transducers 204a-n are in physical contact with body 202 of the subject. For example, receiver 208 and transducers 204a-n may be touching the epidermis of the subject at the wrist. Transducers 204a-n are used to transmit signals 206a-n into body 202. Signals 206a-n may include, but are not limited to: radio frequency (RF) signals, vibrations, audio signals, which may or may not be in the human audible range (e.g., low frequency audio), and/or ultrasound signals. In at least one embodiment, each transmission (e.g., signal 206a) transmitted by a transducer (e.g., transducer 204a) includes more than one signal, with each signal being transmitted at a different frequency and/or output strength (amplitude). For example, signal 206a may include a first sine waveform that is transmitted by transducer 204a at a frequency of 10 hertz (Hz) and a second sine waveform that is transmitted by transducer 204a at 2 megahertz (MHz). In another embodiment, signals 206a-n can include at least one pulse signal. It should be noted that, in at least one embodiment, transmissions(s) (e.g., signal 206a) transmitted by a first transducer (e.g., transducer 204a) are different from transmission(s) (e.g., signal 206a) transmitted by a second transducer (e.g., transducer 204n). Signals 206a-n can be transmitted by transceivers 204a-n during a same time period or a different time period. For example, CPU 104 may transmit signal 206a by transducer 204a during a first 2-second time period and may transmit signal 206n (which is a same or different signal as signal 206a) by transducer 204n during a second 2-second time period that is different from the first 2-second time period. In another example, CPU 104 may transmit signal 206a by transducer 204a and transmit signal 206n (which is different than signal 206a) by transducer 204n during the same 2-second time period.

In the embodiments that use bone conduction detection, receiver 208 measures orientation input 214, which includes signals 206a-n'. Signals 206a-n' are signals 206a-n transmitted by transducers 204a-n into body 202 through an epidermis and at least one bone of the subject. In one or more embodiments, signals 206a-n' may pass through artificial materials such as articles of clothing and/or prosthetic body parts. CPU 104 determines characteristics 218a-n of signals 206a-n' in orientation input 214. Measured characteristics 218a-n may include, but are not limited to, a frequency, phase shift, amplitude, quality, noise, and/or distortion within signals 206a-n'. For example, CPU 104 may compute a phase shift of signal 206a' and an amplitude of signal 206a' at a plurality of frequencies. The type, size, density, and composition of bone and the skin layer will affect characteristics of signals 206a-n as they pass through the body from a transducer to a receiver. CPU 104 analyzes the measured characteristics 218a-n to determine whether the at least one of signals 206a-n' include characteristics that correspond to a passage of the at least one of signals 206a-n through at least one bone of a subject. If the analysis does not conclusively determine that at least one of signals 206a-n has passed through at least one bone of the subject, CPU 104 may re-transmit signals 206a-n into body 202 by transducers 204a-n and re-measure orientation input 214 via receiver 208. In response to being unable to determine whether at least one of signals 206a-n has passed through at least one bone of the subject after a predetermined number of attempts, CPU 104 may present an error message on display 145 that indicates that current orientation 220 and current location 222 of wearable device 100 was unable to be determined. The error message may also include a notification or message that requests a user of wearable device 100 manually select the current orientation 220 and current location 222.

In response to the analysis indicating at least one of signals 206a-n has passed through at least one bone of the subject, CPU 104 accesses signal conduction profiles 224a-n. In at least one embodiment, each of signal conduction profiles 224a-n includes a signature of at least one signal and associates the signature with a particular body location and orientation of wearable device 100. For example, signal conduction profiles 224a may establish a first signature that contains characteristics of the passage of signal 206a from transducer 204a to receiver 208 through the ulna bone of an arm and a second signature that contains characteristics of the passage of signal 206n from transducer 204n to receiver 208 through the radius bone of an arm. In another example, signal conduction profiles 224b may establish a first signature that contains characteristics of the passage of signal 206a from transducer 204a to receiver 208 through the tibia bone of a leg and a second signature that contains characteristics of the passage of signal 206n from transducer 204n to receiver 208 through the fibula bone of a leg.

In another embodiment, signal conduction profiles 224a-n describe expected differences, such an expected phase shift, between a transmitted signal (signal 206a) and a corresponding measured signal (signal 206a') for a particular orientation and/or body location of wearable device 100. It should be noted that each signal conduction profile 224a-n may contain multiple signatures for each signal. For example, signal conduction profile 224a may contain three different signatures that each describe different characteristics of the passage of signal 206a from transducer 204a to receiver 208 through the ulna bone of an arm. CPU 104 compares characteristics 218a-n to signal characteristics of each signal conduction profile 224a-n to determine a signal conduction profile that contains characteristics that mostly closely match characteristics 218a-n. In response to determining a closest match from among signal conduction profiles 224a-n, based on characteristics 218a-n, CPU 104 determines current orientation 220 and current location 222 of wearable device 100 on body 202.

For example, CPU 104 compares characteristics 218a of signal 206a to signal conduction profiles 224a-n and determines that signal 206a corresponds to a signal transmission through an ulna bone of an arm. In this example, CPU 104 compares characteristics 218n of signal 206n to signal conduction profiles 224a-n and determines that signal 206n corresponds to a signal transmission through a radius bone of an arm. Based on the comparisons of characteristics 218a-n to signal conduction profiles 224a-n, CPU 104 determines that wearable device 100 is located on a wrist of the subject. Additionally, based on determining that signal 206a corresponds to a signal transmission through an ulna bone of an arm and signal 206n corresponds to a signal transmission through a radius bone of an arm, CPU 104 determines that wearable device 100 is in an upright orientation.

Infrared Light Detection

In at least one embodiment, wearable device 100 includes a plurality of IR proximity modules 210a-n for determining a current orientation 220 and current location 222 of wearable device 100 on body 202 via infrared light detection. IR proximity modules 210a-n include at least one emitter that projects IR signals 212a-n within a predetermined range/angle onto a surface of body 202 and at least one receiver that receives IR return signals 216a-n, which are reflections of IR signals 212a-n off body 202 of the subject. In one or more embodiments, in response to receiving IR return signals 216a-n, CPU 104 computes a time of flight (ToF) associated with IR signals 212a-n and IR return signals 216a-n. In one or more embodiments, CPU 104 further analyzes the ToF data to determine current orientation 220 and current location 222 of wearable device 100 on body 202.

Figure 4:
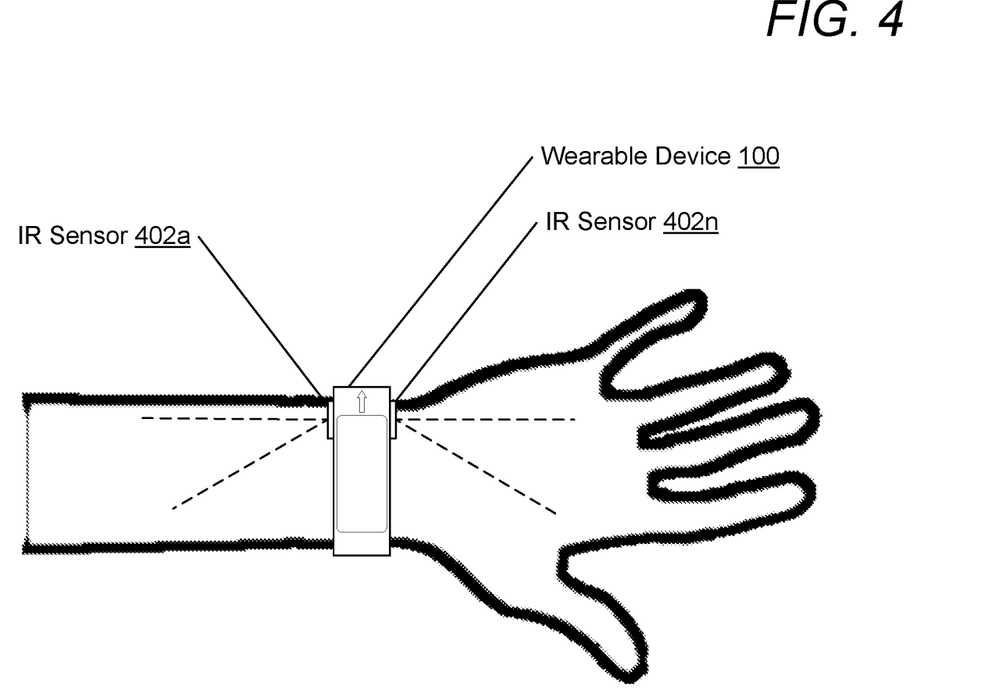
FIG. 4 illustrates a wearable device having a first IR sensor and a second IR sensor and which is worn on a wrist of a subject, in accordance with one or more embodiments of the disclosure.

Referring now to FIG. 4, there is an example illustration of wearable device 100 having a first IR sensor (IR sensor 402a) and a second IR sensor (IR sensor 402n). Wearable device 100 is worn on a wrist of a subject. As illustrated, the first IR sensor is attached to a first side of wearable device 100 and aligned in a first direction. The second IR sensor is attached to a second side of wearable device 100 and aligned in a second direction that is opposite the first direction. As worn in the illustrated example of FIG. 4, IR sensor 402a projects IR light up the arm of the subject while IR sensor 402n projects IR light in the opposite direction, towards the hand of the subject. IR sensor 402a-n receive IR return signals that are reflections of the projected projects IR light.

Referring again to FIG. 2, in the embodiments that use infrared light detection, CPU 104 projects IR signals 212a-n via IR proximity modules 210a-n. IR proximity modules 210a-n receive orientation input 214, which includes IR return signals 216a-n that are reflections of IR signals 212a-n off body 202 of the subject. For example, IR proximity module 210a projects IR signals 212a and also receives IR return signals 216a. In one or more embodiments, CPU 104 analyzes ToF data associated with IR return signals 216a-n to determine at least one estimated distance measurement to body 200 of the subject. For example, in the illustrated embodiment, return signal 216n may be analyzed to determine ToF measurements. The ToF measurements may then be used to estimate distances to at least one knuckle on the hand of the subject.

In response to receiving orientation input 214 (which includes IR return signals 216a-n), CPU 104 accesses IR profiles 226a-n. In at least one embodiment, each of IR profiles 226a-n describes a profile of return signals associated with IR proximity modules 210a-n and a particular body location and orientation of wearable device 100. In one or more embodiments, IR profiles 226a-n may contain estimated distances and/or distance ranges to a particular body part, such as knuckles on a hand of a subject. In other embodiments, IR profiles may contain estimated distances to other body parts, such as measurements to elbows, ankles, ears, feet, and/or knees. In one or more embodiments, IR profile 226a-n include a range of measurements that account for anatomic variations between a variety of subjects. In another embodiment, IR profiles 226a-n may contain multiple signal profiles and/or at least one average return signal profile for particular IR signals projected by IR proximity modules 210a-n. For example, IR profile 226a may be associated with a left hand upright wrist position of wearable device 100 and includes (1) a first profile that describes return distances and/or expected ToF data for IR signal 212a projected by IR proximity modules 210a up the arm of a subject and (2) a second profile that describes return distances and/or expected ToF data for IR signal 212n projected by IR proximity modules 210n towards the hand of the subject, such as measurements to one or more knuckles of a hand. In another example, IR profile 226b may be associated with a right hand upright wrist position of wearable device 100 and includes (1) a first profile that describes return distances and/or expected ToF data for IR signal 212n projected by IR proximity modules 210n up the arm of a subject and (2) a second profile that describes return distances and/or expected ToF data for IR signal 212a projected by IR proximity modules 210a towards the hand of the subject. In another example, IR profile 226n may be associated with first orientation of wearable device 100 on an ankle of a subject and includes (1) a first profile that describes return distances and/or expected ToF data for IR signal 212a projected by IR proximity modules 210a up the leg of a subject and (2) a second profile that describes return distances and/or expected ToF data for IR signal 212n projected by IR proximity modules 210n towards the foot of the subject.

CPU 104 compares the ToF data and/or estimated distance measurements associated with IR return signals 216a-n of IR profiles 226a-n to determine an IR profile that mostly closely matches ToF data and/or distance measurements of IR return signals 216a-n. In response to determining a closest match from among IR profiles 226a-n, CPU 104 determines current orientation 220 and current location 222 of wearable device 100 on body 202 based on the closest matching IR profile. For example, CPU 104 may determine, based on the ToF data and/or estimated distances associated with IR return signal 216a, that IR proximity module 210a is projecting IR signal 212a towards a longer side of a body location, such as an arm. CPU 104 may then determine based on the ToF data and/or estimated distances calculated from IR return signals 216a-n, that wearable device 100 is either being worn in a left hand upright orientation on a left wrist of a subject or a right hand reverse orientation on a right wrist of the subject. CPU 104 may then compare the estimated measurements (and/or ToF data associated with the reflected IR signals) associated with IR return signal 216n to measurements contained in IR profiles 226a-n. For example, IR profile 226a may include measurements and/or measurement ranges to knuckles of a subject when wearable device 100 is worn in a particular orientation (e.g., reverse orientation) and/or at a particular body part (e.g., right hand) of a subject. The estimated measurements associated with IR return signal 216n may be compared to the estimated distances and/or distance ranges within IR profiles 226a-n. For example, during the comparison CPU 104 may determine that (1) a closest estimated measurement in the range of IR return signals 216n corresponds to a measurement within IR profile 226a that is associated with a measurement to a knuckle of an index finger and (2) a farthest estimated measurement in the range of IR return signals 216n corresponds to a measurement within IR profile 226a that is associated with a measurement to a knuckle of a little (pinky) finger. In response to determining the closest knuckle is the knuckle of the index finger, CPU 104 can determine that wearable device 100 is currently being worn in a right hand reverse orientation on a right wrist of the subject. Alternatively, if CPU 104 had determined that the closest knuckle is the knuckle of the little finger, CPU 104 would determine that wearable device 100 is currently being worn in a left hand upright orientation on a left wrist of a subject.

Reconfiguring Input or Output Devices

In response to determining current orientation 220 and current location 222 of wearable device 100 on body 202, CPU 104 configures at least one output device of wearable device 100 for operation at the determined current orientation 220 and current location 222. For example, in a right hand upright orientation, display 145 is configured to display a user interface in a first orientation. In response to determining that wearable device 100 is being worn in a right hand reverse orientation, CPU 104 may rotate the user interface 180 degrees such that user interface can be properly viewed by a user wearing wearable device 100 in the right hand reverse orientation.

In another embodiment, CPU 104 may also configure one or more input devices of wearable device 100 for operation at current orientation 220 and current location 222. For example, in a left hand upright orientation, input button 106a is associated with a volume up function and input button 106n is associated with a volume down function. In response to determining that wearable device 100 is being worn in a left hand reverse orientation, CPU 104 may reconfigure input buttons 106a-n such that input button 106a is associated with a volume down function and input button 106n is associated with a volume up function. In another embodiment, CPU 104 can reconfigure one or more sensors, such as a heart rate sensor for operation at current orientation 220 and current location 222.

It should be noted that in embodiments where wearable device 100 includes both (i) transducers 204a-n and receiver 208 and (ii) IR proximity modules 210a-n, CPU 104 may determine current orientation 220 and current location 222 using a combination of bone conduction detection methods and infrared light detection methods. In one embodiment, CPU 104 separately determines an estimated current orientation and current location of wearable device via the bone conduction detection methods and infrared light detection methods described above. In this embodiment, CPU 104 determines whether the estimated current orientation and current location determined by bone conduction detection matches the estimated current orientation and current location determined by infrared light detection. If the two methods identify a same estimated current orientation and current location, CPU 104 reconfigures at least one input device and/or at least one output device of wearable device 100 based on the determined current orientation 220 and current location 222. In another embodiment, one of the two detection methods is associated with a higher priority. In this embodiment, if the two methods do not identify a same estimated current orientation and current location, CPU 104 may identify an estimated current orientation and current location associated with the higher priority detection method (e.g., bone conduction detection) as current orientation 220 and current location 222 of wearable device 100. In still another embodiment, if the two methods do not identify a same estimated current orientation and current location, CPU 104 may present, an error message on display 145 that indicates that current orientation 220 and current location 222 of wearable device 100 was unable to be determined. CPU 104 may also present a message and/or notification that requests a user of wearable device 100 to manually select the current orientation 220 and current location 222.

Updating Stored Profiles

In one or more embodiments, the analysis of characteristics 218a-n and/or IR return signals 216a-n can be used to generate new signal conduction profiles 224a-n and/or IR profiles 226a-n or improve existing signal conduction profiles 224a-n and/or IR profiles 226a-n. In response to determining current orientation 220 and current location 222 of wearable device 100 on body 202, CPU 104 may store characteristics 218a-n and/or measurements associated with IR return signals 216a-n in a corresponding profile within remote database 230 or a local storage (e.g., memory 110). In another embodiment, in the event CPU 104 is unable to determine current orientation 220 and current location 222 of wearable device 100, CPU 104 may store characteristics 218a-n and/or measurements associated with IR return signals 216a-n within a new profile in remote database 230. In one or more embodiments, remote database 230 is accessible by other wearable devices (not illustrated) and each wearable device may access signal conduction profiles 224a-n and/or IR profiles 226a-n from remote database 230. Additionally, each wearable device may store locally analyzed characteristics 218a-n and measurements associated with IR return signals 216a-n. Locally analyzed characteristics 218a-n may be associated with existing profiles (signal conduction profiles 224a-n and/or IR profiles 226a-n) in local storage (e.g., memory 110). Each wearable device may also forward characteristics 218a-n and/or measurements associated with IR return signals 216a-n to remote database 230. Forwarded characteristics may be stored within new profiles created in remote database 230 and/or may be associated with existing profiles. Thus, any wearable device that can access remote database 230 may utilize analysis data collected by other remote databases to improve future detection of current orientation 220 and current location 222.

Figure 5:
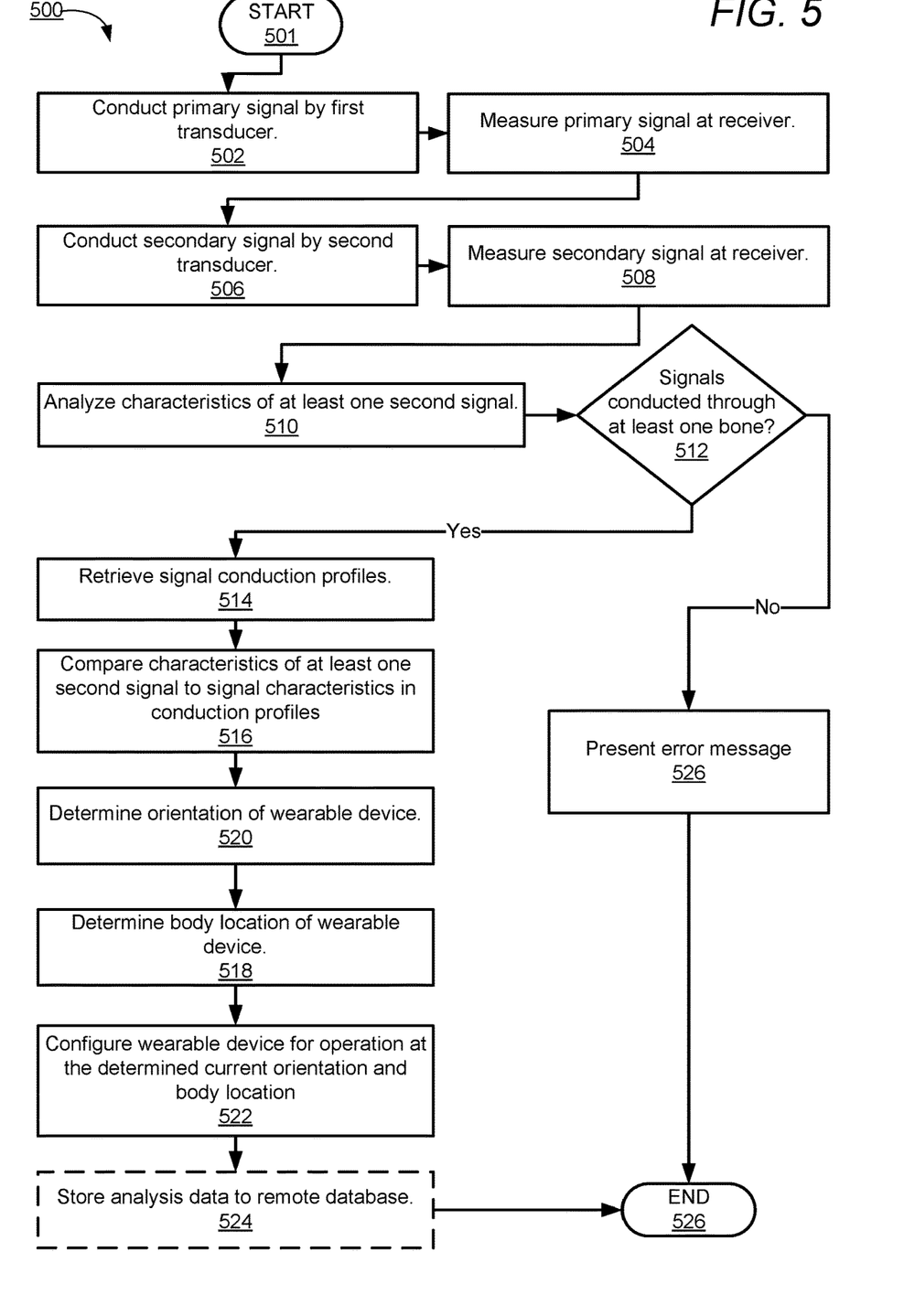
FIG. 5 is a flow chart illustrating a method for using bone conduction to configure a wearable device for a particular orientation and body location, in accordance with one or more embodiments.

Referring now to FIG. 5, there is depicted a high-level flow-chart illustrating a method for using bone conduction to configure a wearable device for a particular orientation and body location, in accordance with one or more embodiments of the present disclosure. Aspects of the method are described with reference to the components of FIGS. 1 and 2. Several of the processes of the method provided in FIG. 5 can be implemented by a processor (e.g., CPU 104) executing software code of BOU 117 within a wearable device (e.g., wearable device 100). The method processes described in FIG. 5 are generally described as being performed by components of wearable device 100.

Method 500 commences at initiator block 501 then proceeds to block 502. At block 502, wearable device 100 transmits a primary signal (signal 206a) by a first transducer (transducer 204a) into body 200 of a subject. At block 504, CPU 104 measures, via receiver 208, a return signal (signal 206a'). For example, CPU 104 may measure a phase shift between signal 206a and signal 206a' and/or an amplitude of signal 206a' at a single frequency or a plurality of frequencies. At block 506, wearable device 100 transmits a secondary signal (signal 206n) by a second transducer (transducer 204a) into body 200 of a subject. At block 508, CPU 104 measures, via receiver 208, a second return signal (signal 206n'). For example, CPU 104 may measure a phase shift between signal 206n and signal 206n' and/or an amplitude of signal 206a' at a single frequency or a plurality of frequencies. At block 510, CPU 104 analyzes the first and second return signals to identify characteristics 218a-n (e.g., amplitude and/or signal quality) within those return signals. At block 512, CPU 104 determines, based on characteristics 218a-n, whether at least one signal has passed through the body and at least one bone of the subject. In response to determining neither of the first and second return signals passed through the body and at least one bone of the subject, CPU 104 presents an error message on an output device (e.g., display 145) that indicates that current orientation 220 and current location 222 of wearable device 100 was unable to be determined. CPU 104 may also present a message and/or notification that requests a user of wearable device 100 to manually select the current orientation 220 and current location 222 (block 526).

In response to determining at block 512 that at least one signal has passed through the body and at least one bone of the subject, CPU 104 retrieves signal conduction profiles 224a-n (block 514). Signal conduction profiles 224a-n may be retrieved from local storage (e.g., memory 110) or a remote database (e.g., remote database 230). At block 516, CPU 104 compares characteristics (characteristics 218a-n)

of the measured signals 206a-n' to signal characteristics in signal conduction profiles 224a-n. At block 518 CPU 104 determines, based on results of the comparison, a current orientation (current orientation 220) of wearable device 100 of body 202 of the subject. At block 520 CPU 104 determines, based on results of the comparison, a current body location (current location 222) of wearable device 100 of body 202 of the subject. At block 522, CPU 104 configures at least one input device and/or output device of wearable device 100 for operation at the determined current orientation and current body location. At block 524, CPU 104 may optionally store analysis data associated with the characteristics (characteristics 218a-n) of the measured signals 206a-n' in a database (e.g., remote database 230). Method 500 then terminates at block 526.

Figure 6:
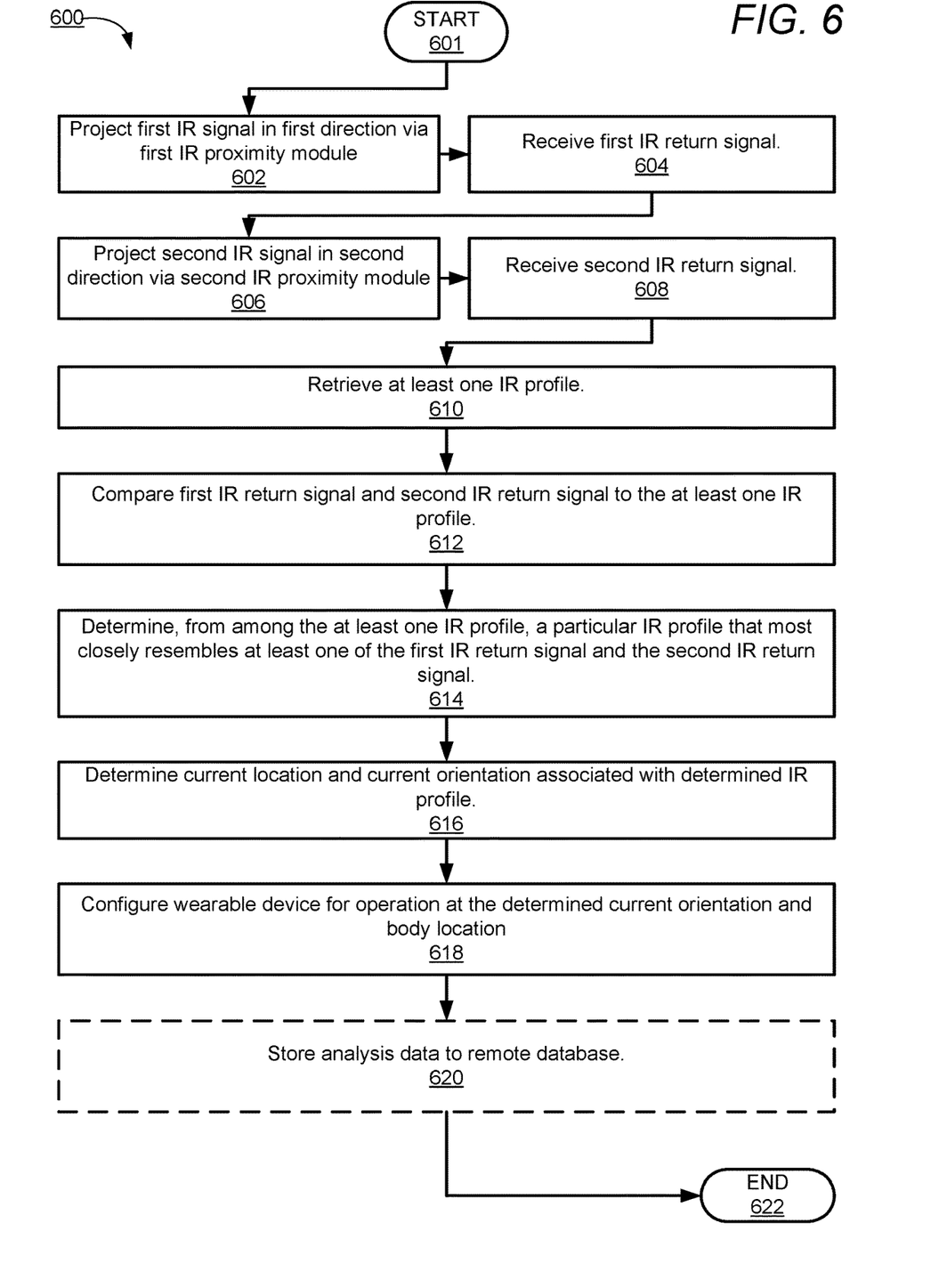
FIG. 6 is a flow chart illustrating a method for using infrared light detection to configure a wearable device for a particular orientation and body location, in accordance with one or more embodiments.

Referring now to FIG. 6, there is depicted a high-level flow-chart illustrating a method for using infrared light detection to configure a wearable device for a particular orientation and body location, in accordance with one or more embodiments of the present disclosure. Aspects of the method are described with reference to the components of FIGS. 1 and 2. Several of the processes of the method provided in FIG. 6 can be implemented by a processor (e.g., CPU 104) executing software code of BOU 117 within a wearable device (e.g., wearable device 100). The method processes described in FIG. 6 are generally described as being performed by components of wearable device 100.

Method 600 commences at initiator block 601 then proceeds to block 602. At block 602, wearable device 100 projects a first IR signal (IR signal 212a) by a first IR proximity module (IR proximity module 210a) in a first direction onto body 202 of a subject. At block 604, CPU 104 receives, via the first IR proximity module, a first IR return signal (IR return signal 216a), which is a reflection of the projected first IR signal. At block 606, wearable device 100 projects a second IR signal (IR signal 212n) by a second IR proximity module (IR proximity module 210n) in a second direction, that is opposite the first direction. At block 608, CPU 104 receives, via the second IR proximity module, a second IR return signal (IR return signal 216n), which is a reflection of the projected second IR signal. At block 610, CPU 104 retrieves IR profiles 226a-n. IR profiles 226a-n may be retrieved from local storage (e.g., memory 110) or a remote database (e.g., remote database 230). At block 612, CPU 104 compares ToF data of IR return signals 212a-n and/or estimated measurements associated with IR return signals 212a-n to measurements within IR profiles 226a-n. At block 614, CPU 104 determines a particular IR profile from among IR profiles 226a-n that includes measurements/measurement ranges and/or ToF data that most closely matches the ToF data and/or estimated measurements associated with IR return signals 212a-n. In response to determining the particular IR profile, CPU 104 identifies a current orientation (current orientation 220) and a current body location (current location 222) of wearable device 100 on the body of the subject (block 616). At block 618, CPU 104 configures at least one input device and/or output device of wearable device 100 for operation at the determined current orientation and current body location. At block 620, CPU 104 may optionally store data associated with the measurements in the IR return signals in a database (e.g., remote database 230). Method 600 then terminates at block 622.

Figure 7:
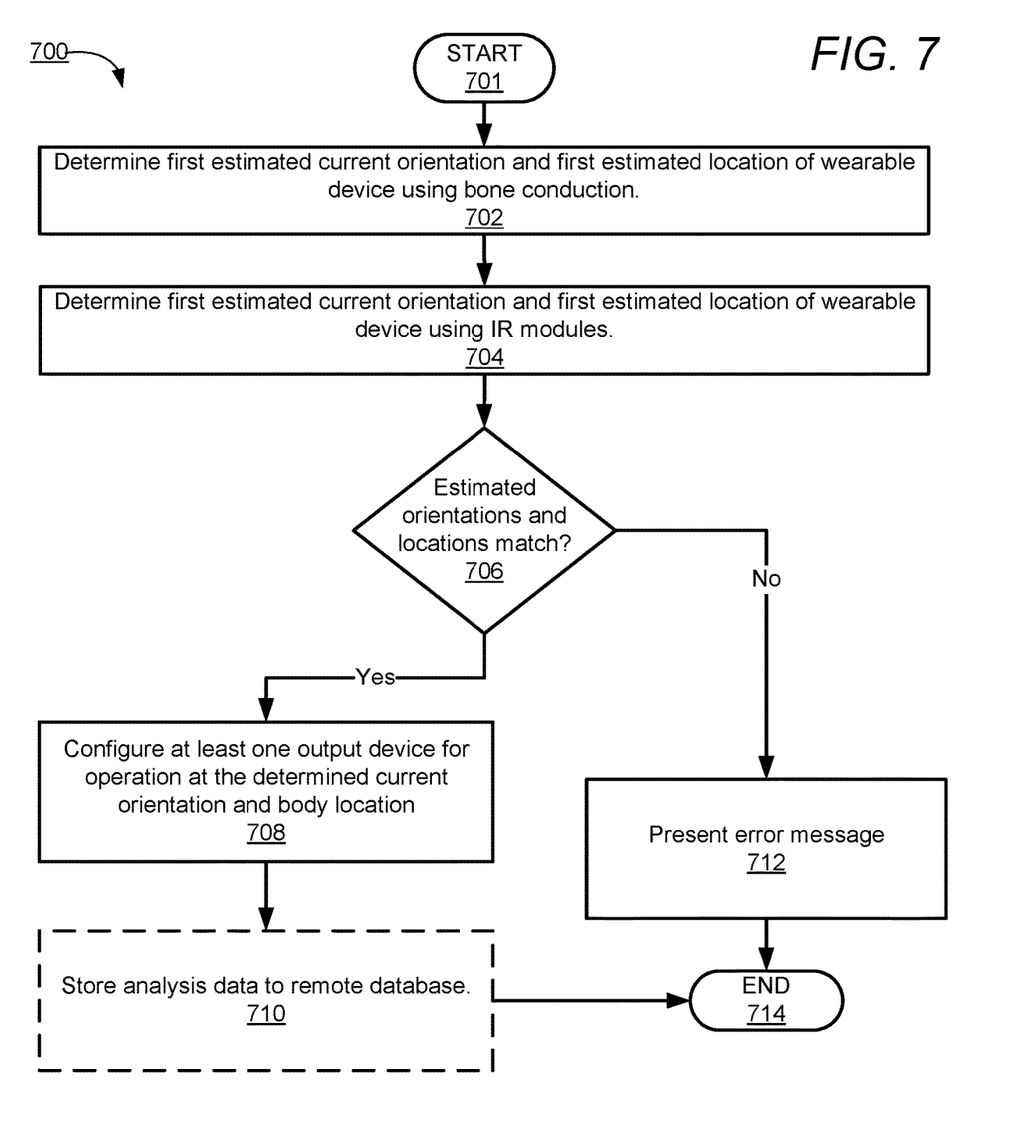
FIG. 7 is a flow chart illustrating a method for using bone conduction and infrared light detection to configure a wearable device for a particular orientation and body location, in accordance with one or more embodiments.

FIG. 7 depicts a high-level flow-chart illustrating a method for using bone conduction and infrared light detection to configure a wearable device for a particular orientation and body location, in accordance with one or more embodiments of the present disclosure. Aspects of the method are described with reference to the components of FIGS. 1 and 2. Several of the processes of the method provided in FIG. 7 can be implemented by a processor (e.g., CPU 104) executing software code of BOU 117 within a wearable device (e.g., wearable device 100). The method processes described in FIG. 7 are generally described as being performed by components of wearable device 100.

Method 700 commences at initiator block 701 then proceeds to block 702. At block 702, CPU 104 determines a first estimated current location and a first estimated current orientation via a bone conduction detection method (such as the bone conduction detection method described in steps 501-518 of FIG. 5). At block 704, CPU 104 determines a second estimated current location and a second estimated current orientation via a IR light detection method (such as the IR light detection method described in steps 601-616 of FIG. 6). At block 706, CPU 104 determines whether the two results (body location and current orientation of wearable device 100) match. That is, CPU 104 determines if the first estimated current location and the first estimated current orientation are the same as the second estimated current location and a second estimated current orientation, respectively.

In response to determining a same body location and same current orientation of wearable device 100 via both the bone conduction detection method and the IR light detection method, CPU 104 configures at least one input device and/or output device of wearable device 100 for operation at the determined current orientation and current body location (block 708). At block 710, CPU 104 may optionally store analysis data associated with the characteristics (characteristics 218a-n) of the measured signals 206a-n' and data associated with the measurements in the IR return signals in a database (e.g., remote database 230). Method 700 then terminates at block 714.

In response to determining that the bone conduction detection and the IR light detection method did not determine a same body location and/or a same current orientation of wearable device 100, CPU 104 provides an error message on an output device (e.g., display 145) that indicates that the current orientation and the current location of wearable device 100 was unable to be determined (block 712). In one embodiment, CPU 104 also presents a notification or message that requests a user of wearable device 100 manually select the current orientation 220 and current location 222 (block 714). Method 700 then terminates at block 716.

In the above-described flow charts of FIG. 5-7, one or more of the method processes may be embodied in a computer readable device containing computer readable code such that a series of steps are performed when the computer readable code is executed on a computing device. In some implementations, certain steps of the methods are combined, performed simultaneously or in a different order, or perhaps omitted, without deviating from the scope of the disclosure. Thus, while the method steps are described and illustrated in a particular sequence, use of a specific sequence of steps is not meant to imply any limitations on the disclosure. Changes may be made with regards to the sequence of steps without departing from the spirit or scope of the present disclosure. Use of a particular sequence is therefore, not to be taken in a limiting sense, and the scope of the present disclosure is defined only by the appended claims.

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. Computer program code for carrying out operations for aspects of the present disclosure may be written in any combination of one or more programming languages, including an object oriented programming language, without limitation. These computer program instructions may be provided to a processor of a general purpose computer, special purpose computer, or other programmable data processing apparatus to produce a machine that performs the method for implementing the functions/acts specified in the flowchart and/or block diagram block or blocks. The methods are implemented when the instructions are executed via the processor of the computer or other programmable data processing apparatus.

As will be further appreciated, the processes in embodiments of the present disclosure may be implemented using any combination of software, firmware, or hardware. Accordingly, aspects of the present disclosure may take the form of an entirely hardware embodiment or an embodiment combining software (including firmware, resident software, micro-code, etc.) and hardware aspects that may all generally be referred to herein as a "circuit," "module," or "system." Furthermore, aspects of the present disclosure may take the form of a computer program product embodied in one or more computer readable storage device(s) having computer readable program code embodied thereon. Any combination of one or more computer readable storage device(s) may be utilized. The computer readable storage device may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage device can include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage device may be any tangible medium that can contain, or store a program for use by or in connection with an instruction execution system, apparatus, or device.

Where utilized herein, the terms "tangible" and "non-transitory" are intended to describe a computer-readable storage medium (or "memory") excluding propagating electromagnetic signals; but are not intended to otherwise limit the type of physical computer-readable storage device that is encompassed by the phrase "computer-readable medium" or memory. For instance, the terms "non-transitory computer readable medium" or "tangible memory" are intended to encompass types of storage devices that do not necessarily store information permanently, including, for example, RAM. Program instructions and data stored on a tangible computer-accessible storage medium in non-transitory form may afterwards be transmitted by transmission media or signals such as electrical, electromagnetic, or digital signals, which may be conveyed via a communication medium such as a network and/or a wireless link.

While the disclosure has been described with reference to example embodiments, it will be understood by those skilled in the art that various changes may be made and equivalents may be substituted for elements thereof without departing from the scope of the disclosure. In addition, many modifications may be made to adapt a particular system, device, or component thereof to the teachings of the disclosure without departing from the scope thereof. Therefore, it is intended that the disclosure not be limited to the particular embodiments disclosed for carrying out this disclosure, but that the disclosure will include all embodiments falling within the scope of the appended claims.

The description of the present disclosure has been presented for purposes of illustration and description, but is not intended to be exhaustive or limited to the disclosure in the form disclosed. Many modifications and variations will be apparent to those of ordinary skill in the art without departing from the scope of the disclosure. The described embodiments were chosen and described in order to best explain the principles of the disclosure and the practical application, and to enable others of ordinary skill in the art to understand the disclosure for various embodiments with various modifications as are suited to the particular use contemplated.

What is claimed is:

1. A method comprising:
receiving at least one orientation input comprising (i) at least one signal transmitted via at least one orientation module of a wearable device and (ii) a corresponding at least one response signal captured via a receiver associated with the orientation module;
analyzing, via a processor of the wearable device, the at least one orientation input to determine:
a body location of the wearable device, the body location being a current location at which the wearable device is being worn on a body of a subject, the body location at least in part determined by a passage of the at least one signal transmitted by a component of the at least one orientation module through a bone of the subject to generate the corresponding at least one response signal, the at least one response signal having characteristics correlated to the passage of the signal through a specific bone within the body of the subject; and
a current orientation of the wearable device at the body location;
wherein: the analyzing comprises:
analyzing a plurality of characteristics of the at least one response signal to determine whether the at least one response signal comprises characteristics that correspond to a passage of the at least one signal through at least one bone of a subject; and
in response to the analysis indicating the at least one signal has passed through the at least one bone of the subject, comparing the plurality of characteristics to a plurality of signal characteristics of at least one signal conduction profile, which comparing establishes a signature of the at least one signal to determine, based on the plurality of characteristics, the body location on the body of the subject and the current orientation of the wearable device; and
configuring at least one output device of the wearable device for operation in the current orientation at the body location.

2. The method of claim 1, wherein the at least one orientation module comprises at least one transducer, the method further comprising:
transmitting, by the at least one transducer of the wearable device, at least one first signal corresponding to the at least one orientation input;

wherein:
receiving the at least one orientation input further comprises receiving, by at least one receiver of the wearable device, at least one second signal within the at least one orientation input, the at least one second signal resulting from a transmission of the at least one first signal.

3. The method of claim 2, further comprising:
retrieving the at least one signal conduction profile from at least one remote database; and
in response to identifying the body location and the current orientation of the wearable device, storing, to the at least one remote database, a new signal conduction profile that is associated with the at least one second signal and which includes the plurality of characteristics, to enable the new signal conduction profile to be accessible to other wearable devices.

4. The method of claim 1, wherein the at least one orientation input comprises at least a first and a second orientation input and the at least one orientation module comprises:
a first transducer that is positioned at a first location on the wearable device and which conducts a primary signal that results in return of a first return signal of the first orientation input from among the at least one orientation input; and
a second transducer that is positioned at a second location on the wearable device that is different from the first location and which conducts a secondary signal that results in return of a second return signal of the second orientation input from among the at least one orientation input.

5. The method of claim 4, further comprising:
measuring a first amplitude of the primary signal at a plurality of frequencies;
measuring a second amplitude of the secondary signal at the plurality of frequencies; and
determining, based on the first amplitude and the second amplitude at the plurality of frequencies, the body location and the current orientation of the wearable device.

6. The method of claim 1, wherein the at least one orientation module includes:
a first infrared (IR) proximity module that is attached to a first side of the wearable device and aligned in a first direction; and
a second IR proximity module that is attached to a second side of the wearable device and aligned in a second direction that is opposite the first direction.

7. The method of claim 6, further comprising:
projecting, via the first IR proximity module, a first IR signal in the first direction;
projecting, via the second IR proximity module, a second IR signal in the second direction;
receiving, via the first IR proximity module, a first IR return signal that is used to determine a first distance to the body of the subject;
receiving, via the second IR proximity module, a second IR return signal that is used to determine a second distance to the body of the subject; and
determining, based in part on a time of flight of the first IR return signal and a time of flight of the second IR return signal corresponding to an IR profile, the body location on the body of the subject and the current orientation of the wearable device.

8. The method of claim 7, wherein the at least one orientation input includes the first IR return signal and the second IR return signal, and wherein analyzing the first IR return signal and the second IR return signal further comprises:
retrieving at least one IR profile that describes at least one average return signal that is associated with a particular body location and a particular orientation of the wearable device;
comparing the first IR return signal and the second IR return signal to the at least one IR profile;
identifying, from among the at least one IR profile, a particular IR profile that describes the at least one average return signal that resembles at least one of the first IR return signal and the second IR return signal; and
determining the body location and the current orientation of the wearable device based on the particular IR profile.

9. A wearable device comprising:
at least one orientation module that transmits at least one signal used to measure at least one orientation input;
at least one receiver that receives at least one response signal corresponding to the at least one signal; and
at least one processor that:
receives the at least one orientation input from the at least one orientation module and the corresponding at least one response signal used to measure at least one orientation input;
analyzes the at least one orientation input and the corresponding at least one response signal to determine:
a body location of the wearable device, the body location being a current location at which the wearable device is being worn on a body of a subject, the body location at least in part determined by a passage of the at least one signal transmitted by the at least one orientation module through a bone of the subject to generate the response signal, the response signal having characteristics correlated to the passage of the signal through a specific bone within the body of the subject; and
a current orientation of the wearable device at the body location; and
configures at least one output device of the wearable device for operation in the current orientation at the body location;
wherein to analyze the at least one orientation input, the processor:
analyzes a plurality of characteristics of the at least one second signal to determine whether the at least one second signal comprises characteristics that correspond to a passage of the at least one first signal through at least one bone of the subject; and
in response to the analysis indicating the at least one first signal has passed through the at least one bone of the subject, compares the plurality of characteristics to a plurality of signal characteristics of at least one signal conduction profile, which comparison establishes a signature of the at least one first signal to determine, based on the plurality of characteristics, the body location on the body of the subject and the current orientation of the wearable device.

10. The wearable device of claim 9, wherein:
the at least one orientation module includes:
   at least one transducer that conducts at least one first signal that results in the at least one orientation input; and
   at least one receiver that measures the at least one orientation input, which includes at least one second signal.

11. The wearable device of claim 10, further comprising:
a network interface that:
   retrieves the at least one signal conduction profile from at least one remote database; and
   in response to identifying the body location and the current orientation of the wearable device, transmits, to the at least one remote database, a new signal conduction profile that is associated with the at least one second signal and which includes the plurality of characteristics, to enable the new signal conduction profile to be accessible to other wearable devices.

12. The wearable device of claim 9, wherein:
the at least one orientation input comprises at least a first and a second orientation input; and
the at least one orientation module comprises:
a first transducer that is positioned at a first location on the wearable device and which conducts a primary signal that results in return of a first return signal of the first orientation input from among the at least one orientation input; and
a second transducer that is positioned at a second location on the wearable device that is different from the first location and which conducts a secondary signal that results in return of a second return signal of the second orientation input from among the at least one orientation input.

13. The wearable device of claim 12, wherein:
the at least one orientation module further comprises at least one receiver that measures the primary signal and the secondary signal of the at least one orientation input; and
the processor:
   determines a first amplitude of the primary signal at a plurality of frequencies;
   determines a second amplitude of the secondary signal at the plurality of frequencies; and
   determines, based on the first amplitude and the second amplitude at the plurality of frequencies, the body location and the current orientation of the wearable device.

14. The wearable device of claim 9, wherein the at least one orientation module includes:
   a first infrared (IR) proximity module that is attached to a first side of the wearable device and aligned in a first direction; and
   a second IR proximity module that is attached to a second side of the wearable device and aligned in a second direction that is opposite the first direction.

15. The wearable device of claim 14, wherein:
the first IR proximity module:
   projects a first IR signal in the first direction onto a first location on a body of the subject; and
   receives a first IR return signal;
the second IR proximity module:
   projects a second IR signal in the second direction onto a second location on the body of the subject; and
   receives a second IR return signal; and
the processor determines, based in part on a time of flight of the first IR return signal and a time of flight of the second IR return signal corresponding to an IR profile, the body location on the body of the subject and the current orientation of the wearable device.

16. The wearable device of claim 15, wherein:
the at least one orientation input includes the first IR return signal and the second IR return signal; and
in analyzing the first IR return signal and the second IR return signal, the processor:
   retrieves at least one IR profile that describes at least one average return signal that is associated with a particular body location and a particular orientation of the wearable device;
   compares the first IR return signal and the second IR return signal to the at least one IR profile;
   identifies, from among the at least one IR profile, a particular IR profile that describes the at least one average return signal that resembles at least one of the first IR return signal and the second IR return signal; and
   determines the body location and the current orientation of the wearable device based on the particular IR profile.

17. The wearable device of claim 9, wherein the chassis of the wearable device is contoured in a physical shape that is adapted for wearing on a human body with one surface aligned adjacent to an epidermis of the human body when properly worn.

18. A computer program product comprising:
a non-transient computer readable storage medium; and
program code on the computer readable storage medium that, when executed by a processor associated with a wearable device, enables the wearable device to provide the functionality of:
   receiving at least one orientation input comprising (i) at least one signal transmitted via at least one orientation module of a wearable device and (ii) a corresponding at least one response signal captured via a receiver associated with the orientation module;
   analyzing, via a processor of the wearable device, the at least one orientation input to determine:
      a body location of the wearable device, the body location being a current location at which the wearable device is being worn on a body of a subject, the body location at least in part determined by a passage of the at least one signal transmitted by a component of the at least one orientation module through a bone of the subject to generate the corresponding at least one response signal, the at least one response signal having characteristics correlated to the passage of the signal through a specific bone within the body of the subject; and
      a current orientation of the wearable device at the location;
   wherein the analyzing comprises:
      analyzing a plurality of characteristics of the at least one response signal to determine whether the at least one response signal comprises characteristics that correspond to a passage of the at least one signal through at least one bone of a subject; and
      in response to the analysis indicating the at least one signal has passed through the at least one bone of the subject, comparing the plurality of characteristics to a plurality of signal characteristics of at least one signal conduction profile, which comparing establishes a signature of the at least one signal to determine, based on the plurality of characteristics, the body location on the body of the subject and the current orientation of the wearable device; and configuring at least one output device of the wearable device for operation in the current orientation at the body location.

19. The computer program product of claim 18, the program code further comprising code for:

conducting, by at least one transducer of the wearable device, at least one first signal that results in a corresponding at least one response signal of the at least one orientation input, wherein:

the program code for receiving the at least one orientation input further comprises program code for receiving, by at least one receiver of the wearable device, the at least one orientation input including at least one second signal.

20. The computer program product of claim 18, wherein:
the at least one orientation module includes:

a first infrared (IR) proximity module that is attached to a first side of the wearable device and aligned in a first direction; and a second IR proximity module that is attached to a second side of the wearable device and aligned in a second direction that is opposite the first direction;

the program code further comprising code for:

projecting, via the first IR proximity module, a first IR signal in the first direction;

projecting, via the second IR proximity module, a second IR signal in the second direction;

receiving, via the first IR proximity module, a first IR return signal that is used to determine a first distance to a body of the subject;

receiving, via the second IR proximity module, a second IR return signal that is used to determine a second distance to the body of the subject; and determining, based on a time of flight of the first IR return signal and a time of flight of the second IR return signal corresponding to at least one IR profile, the body location on the body of the subject and the current orientation of the wearable device.

\* \* \* \* \*